(12) United States Patent
Park et al.

(10) Patent No.: US 8,197,522 B2
(45) Date of Patent: Jun. 12, 2012

(54) PEDICLE SCREW AND OPERATING DEVICE THEREOF

(75) Inventors: Keun Ho Park, Jeonju-si (KR); Jong Myeon Choi, Suwon-si (KR); Hoon Lee, Jeju-si (KR)

(73) Assignees: Solco Biomedical Co., Ltd., Pyeongtaeg-si (KR); Keun Ho Park, Jeonju-si (KR)

( * ) Notice: Subject to any disclaimer, the term of this patent is extended or adjusted under 35 U.S.C. 154(b) by 851 days.

(21) Appl. No.: 12/061,326

(22) Filed: Apr. 2, 2008

(65) Prior Publication Data

US 2008/0183222 A1   Jul. 31, 2008

Related U.S. Application Data

(62) Division of application No. 10/954,227, filed on Oct. 1, 2004, now Pat. No. 7,871,413.

(30) Foreign Application Priority Data

Jul. 21, 2004   (KR) .................. 10-2004-0056911
Jul. 21, 2004   (KR) .................. 10-2004-0056912

(51) Int. Cl.
   *A61B 17/88*   (2006.01)

(52) U.S. Cl. ............................................. 606/305
(58) Field of Classification Search .......... 606/300–320; 411/190, 337, 439, 511, 955
See application file for complete search history.

(56) References Cited

U.S. PATENT DOCUMENTS

| | | | |
|---|---|---|---|
| 6,530,929 B1 | 3/2003 | Justis et al. | |
| 7,188,626 B2 | 3/2007 | Foley et al. | |
| 7,833,251 B1 * | 11/2010 | Ahlgren et al. | 606/279 |
| 2003/0060826 A1 | 3/2003 | Foley et al. | |
| 2003/0229347 A1 | 12/2003 | Sherman et al. | |

* cited by examiner

*Primary Examiner* — Eduardo C Robert
*Assistant Examiner* — Tara Carter
(74) *Attorney, Agent, or Firm* — LRK Patent Law Firm (57) ABSTRACT

Disclosed is a spine fixation apparatus, more particularly, a pedicle screw implanted into a spine and an operating device for the pedicle screw capable of easily inserting a rod to a head 5 section of the pedicle screw in order to securely fix the spine. The pedicle screw has a head section including a recess part defined by first and second sidewalls, a screw section, and a support unit formed at an upper portion of the recess part of the head section while connecting the first sidewall to the second sidewall.

2 Claims, 12 Drawing Sheets

PEDICLE SCREW AND OPERATING DEVICE THEREOF

CROSS-REFERENCE TO RELATED APPLICATION

This application is a division of U.S. patent application Ser. No. 10/954,227, which was filed on Oct. 1, 2004, the entire subject matter of which is incorporated by reference in its entirety.

BACKGROUND OF THE INVENTION

1. Field of the Invention

The present invention relates to a spine fixation apparatus, and more particularly to a pedicle screw implanted into a spine and an operating device for the pedicle screw capable of easily inserting a rod to a head section of the pedicle screw in order to securely fix the spine.

2. Description of the Prior Art

As generally known in the art a spine fixation apparatus is provided for treating patients who have vertebral disease caused by traffic accidents or fall accidents. For instance, the spine fixation apparatus connects bones forming the spine to each other so as to assist patients with vertebral fracture to be restored to health.

A patient makes a living with a spine fixation apparatus implanted into the spine of the patient. Thus, a subsidiary implanted into a body of the patient must have a simple structure and must not be deformed or released even if the patient takes an active life for a long period of time.

Figure 1:
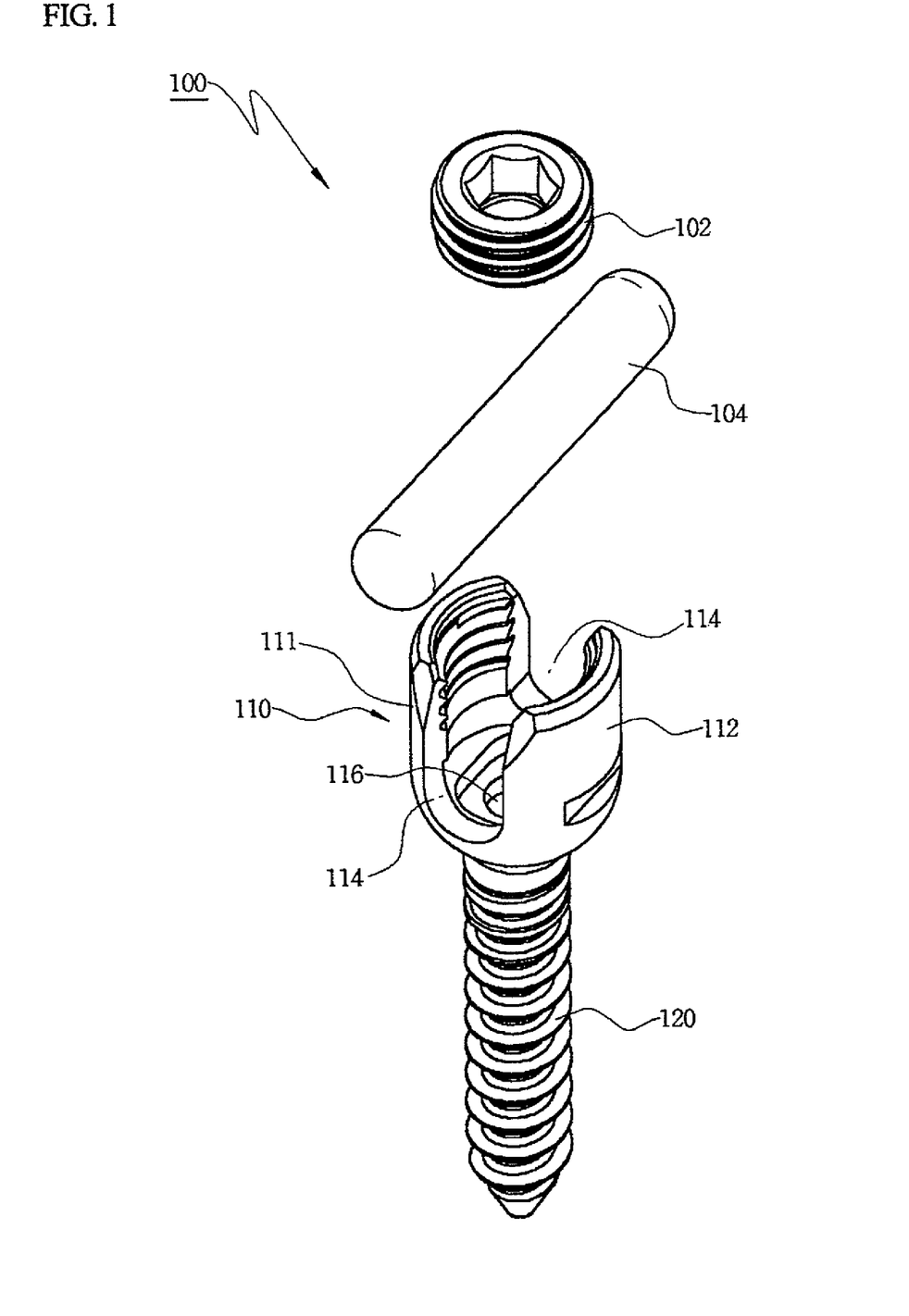
FIG. 1 is a perspective view showing a conventional spine fixation apparatus.

FIG. 1 shows a conventional spine fixation apparatus. Referring to FIG. 1, the conventional spine fixation apparatus includes a pedicle screw 100 provided with a rod 104 and a coupling screw 102 which are coupled to an upper portion of the pedicle screw 100.

The pedicle screw 100 is provided at an upper end thereof with a head section 110 and a lower end thereof with a screw section 120. The rod 104 is inserted into a recess 114 of the head section 110. The recess 114 is defined by first and second sidewalls 111 and 112 and receives the rod 104 therein.

When the rod 104 has been received in the head section 110 of the pedicle screw 100, the coupling screw 102 is screw-coupled into the upper portion of the pedicle screw 100 so as to prevent the rod 104 from being separated from the pedicle screw 100. The first and second sidewalls 111 and 112 of the head section 110 are formed at inner portions thereof with screw sections such that the coupling screw 102 is securely fixed to the head section 110 of the pedicle screw 100.

The screw section 120 of the pedicle screw 100 is screw-coupled into a bone of a spine of a patient so that the pedicle screw 100 is implanted into a body of the patient. The pedicle screw 100 is connected to the other pedicle screw, which is screw-coupled with the other bone of the spine of the patient, through the rod 104.

The rod 104 is inserted into the pedicle screw 100 from an upper portion of the pedicle screw 100 when the pedicle screw 100 is implanted into the patient. Accordingly, it is necessary to make elongated incisions in the patient's back. That is, the back of the patient must be incised corresponding to a length of the rod 104. Reference numeral 116 represents an inner bottom surface of the head section 110.

The current tendency of a surgical operation is to minimize an incision part in a human body. Thus, there has been suggested a method capable of minimizing an incision part in the back of a patient when a pedicle screw is implanted into the body of the patient. According to the above method, a rod is inserted into the pedicle screw from a lateral portion of the pedicle screw instead of inserting the rod from an upper portion of the pedicle screw. In this case, two pedicle screws can be implanted into the body of the patient without incising the back of the patient in a long size by forming only three incisions (two is for pedicle screws and one is for the rod) in the back of the patient.

When the rod is inserted into the pedicle screw from the lateral portion of the pedicle screw, one end of the rod must be easily inserted into a recess part of the pedicle screw. In addition, it is necessary to prevent the rod from being easily separated from the recess part. The rod is inserted into the recess part of a head section of the pedicle screw and fixedly coupled thereto by means of a coupling screw. Accordingly, the rod can be easily separated from the head section of the pedicle screw before the coupling screw is coupled thereto.

For this reason, if the conventional pedicle screw is used for the minimum incision surgery, the pedicle screw may be separated from the pedicle screw while the surgery operation is being carried out, resulting a delay or a failure of the surgery operation.

In addition, since the minimum incision surgery is carried out while making several incisions in the back of the patient while keeping the size of the incisions quite small, a position of the pedicle screw is not exposed to an exterior. Thus, it is difficult to determine a coupling position of a screw section of the pedicle screw having a diameter of about 5 mm with respect to the spine of the patient.

In the meantime, the minimum incision surgery requires great skill when determining the coupling position of the pedicle screw with regard to the spine of the patient and inserting the rod into the pedicle screw from the lateral portion of the pedicle screw. This is because the incisions made in the back of the patient tend to be clogged by skin and the operator cannot see the pedicle screw, which has already been implanted in the body of the patient. Thus, the operator must perform the surgical operation while gripping the pedicle screw with one hand in order to couple the pedicle screw to a precise position of the spine of the patient.

That is, since the minimum incision surgery is carried out while making several incisions in the back of the patient and keeping the size of the incisions quite small the location of the pedicle screw is "subcutaneous", so that the operator cannot easily carry out minimum incision surgery.

Therefore, it is necessary to provide an apparatus to facilitate minimum incision surgery capable of allowing the operator to easily couple a pedicle screw to the spine of the patient and insert a rod into the pedicle screw from a lateral portion of the pedicle screw.

SUMMARY OF THE INVENTION

Accordingly, the present invention has been made to solve the above-mentioned problems occurring in the prior art and an object of the present invention is to provide a pedicle screw including a support unit which connects a first sidewall of a head section to a second sidewall of the head section in order to prevent a rod, which is inserted into the head section of the pedicle screw from a lateral portion of the pedicle screw, from being separated upward from the head section.

Another object of the present invention is to provide a pedicle screw including an indicator protruding from an end of a screw section of the pedicle screw for precisely indicating an insertion point of the pedicle screw during minimum incision surgery.

Still another object of the present invention is to provide an operating device for a pedicle screw allowing an operator to easily perform minimum incision surgery while making several incisions for the pedicle screw and a rod in the back of a patient.

To accomplish the above objects, according to one aspect of the present invention, there is provided a pedicle screw comprising: a head section including a recess part defined by first and second sidewalls; a screw section; and a support unit formed at an upper portion of the recess part of the head section while connecting the first sidewall to the second sidewall.

According to the preferred embodiment of the present invention, the pedicle screw has a guide hole extending from an inner bottom surface of the head section to a lower end portion of the screw section.

To accomplish the above objects, according to another aspect of the present invention, there is provided an operating device for a pedicle screw, the operating device comprising: a screw coupling rod having an elongated pipe shape; a body having a first side coupled to the screw coupling rod; a rotating member having a first end coupled to a second side of the body in such a manner that a second end of the rotating member rotates about the first end thereof, and a rod receiver coupled to the second end of the rotating member.

According to the preferred embodiment of the present invention, the body includes a coupling hole into which the first end of the rotating member is inserted and an elongated rod having a coupling slot for coupling the screw coupling rod.

The screw coupling rod is coupled to the body by means of a coupling member, the elongated rod extends by passing through the coupling member, and the coupling member is provided with a first screw, which is screw-coupled with the coupling slot, and a second screw for supporting the screw coupling rod.

The rod receiver has a curved shape in the form of an arc and the rod is detachably coupled to one end of the rod receiver. The rod receiver is provided at an inner portion thereof with a flexible shaft which is screw-coupled with one end of the rod, and the rod is coupled with or separated from the rod receiver according to a rotational direction of the flexible shaft.

The screw coupling rod has an upper end portion coupled to the body and a lower end portion into which a pedicle screw is inserted. The screw coupling rod is formed at a lower end portion thereof with a rod hole.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, a preferred embodiment of the present invention will be described with reference to the accompanying drawings.

Figure 2:
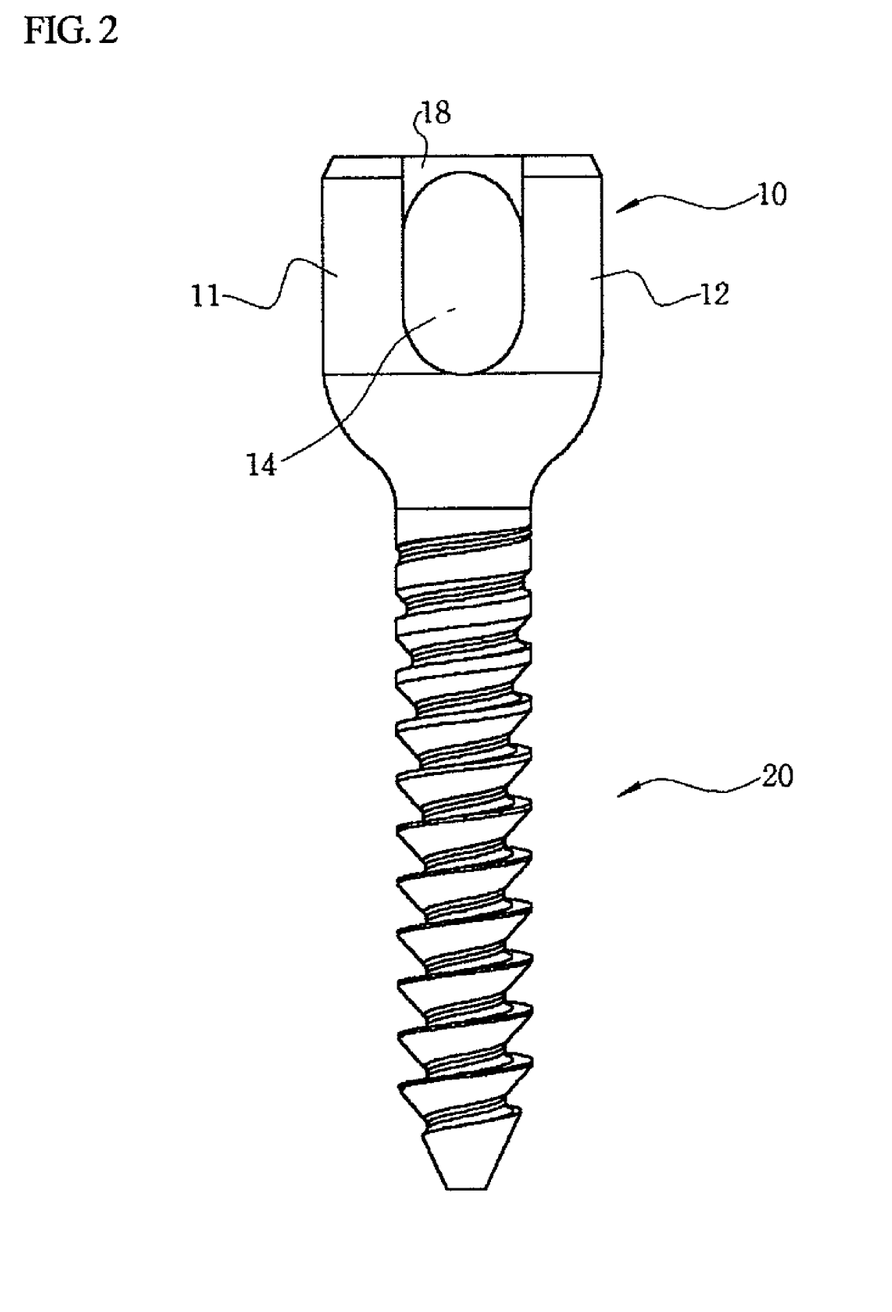
FIG. 2 is a front view of a pedicle screw according to one embodiment of the present invention.
Figure 3:
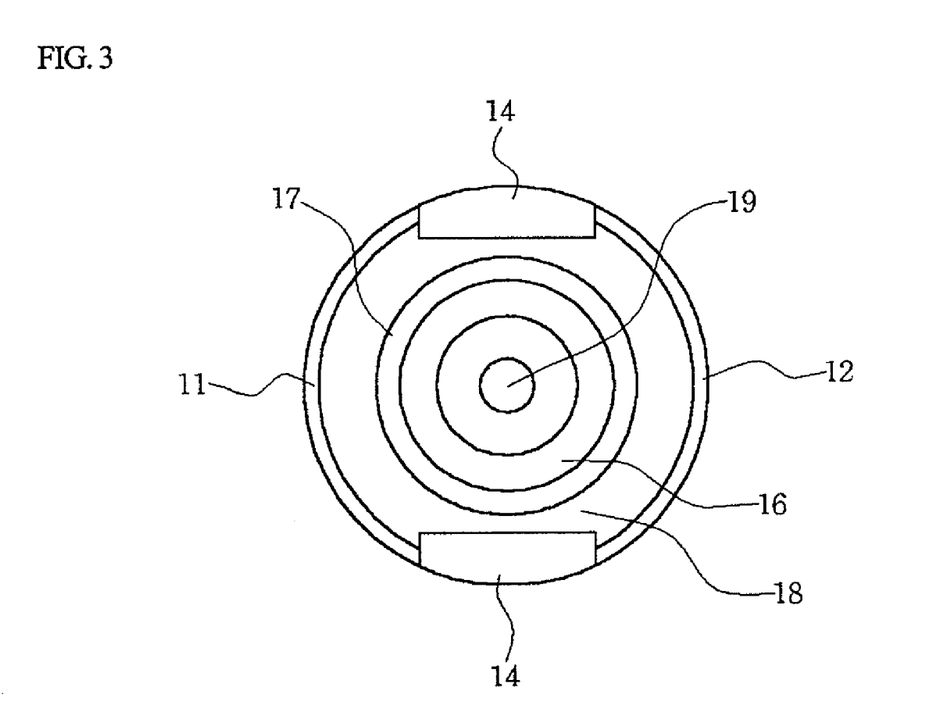
FIG. 3 is a plan view of a pedicle screw according to one embodiment of the present invention.
Figure 4:
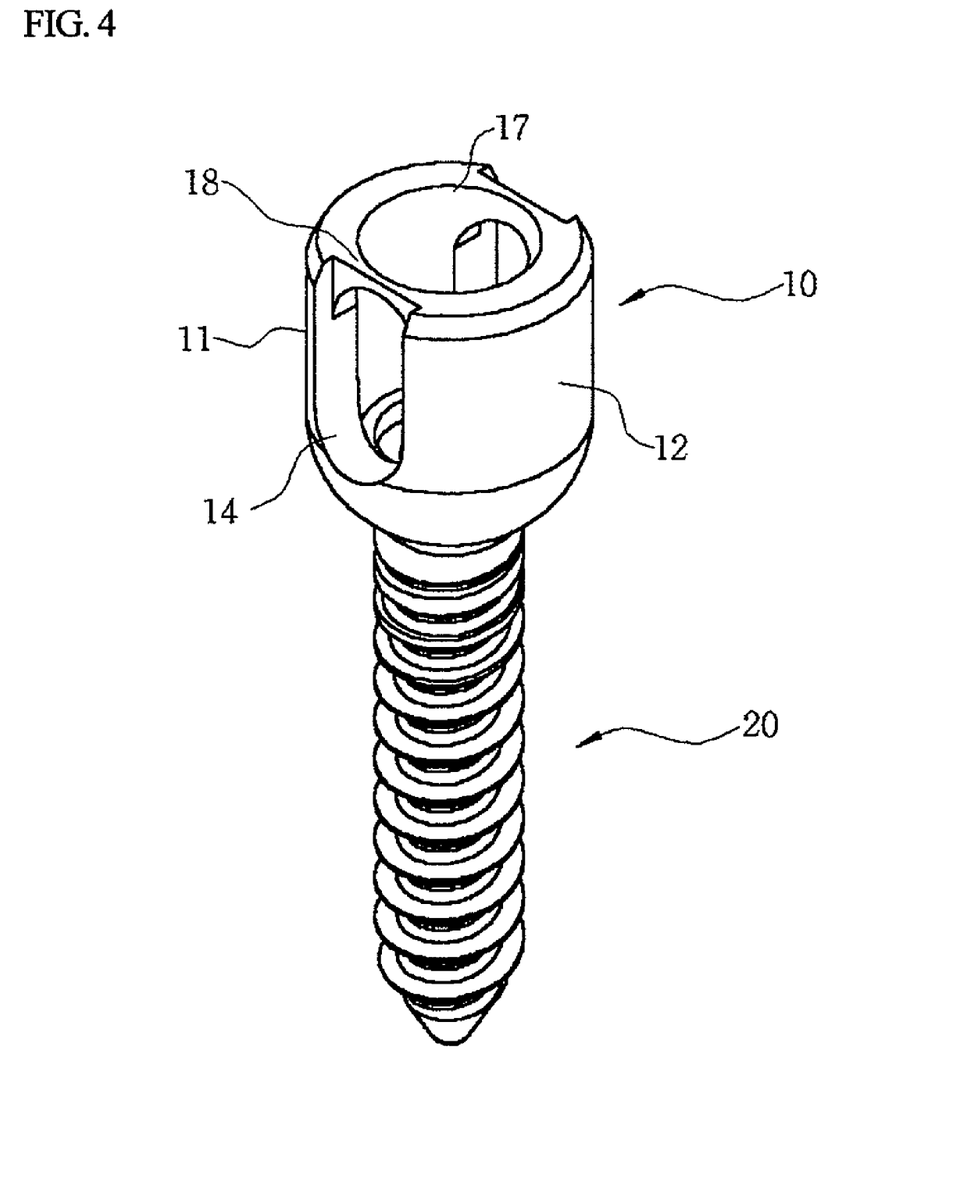
FIG. 4 is a perspective view of a pedicle screw according to one embodiment of the present invention.

FIGS. 2 to 4 are front, plan and perspective views of a pedicle screw according to one embodiment of the present invention Referring to FIGS. 2 to 4, the pedicle screw includes a head section 10 formed with first and second sidewalls 11 and 12. A recess 14 is formed between the first and second sidewalls 11 and 12 and a support unit 18 is formed at an upper portion of the recess 14 in order to connect the first sidewall 11 to the second sidewall 12.

The support unit 18 horizontally connects upper portions of the first and second sidewalls 11 and 12 to each other. Thus, the support unit 18 forms a hole having a predetermined size together with the recess 14. The shape and position of the support unit 18 may vary so far as the support unit 18 connects the first sidewall 11 to the second sidewall 12 and prevents a rod (not shown) from being separated upwardly of the recess 14. As shown in FIG. 3, the recess 14 is formed with a screw hole 17 such that a coupling screw (102, see FIG. 6) can be screw-coupled with the recess 14 from an upper portion of the support unit 18. Since the coupling screw 102 is screw-coupled with the screw hole 17 of the recess 14, the support unit 18 must be aligned such that it does not block a movement path of the coupling screw 102.

A guide hole 19 is formed at a center of an inner bottom surface 17 of the head section 10 formed between the first and second sidewalls 11 and 12 of the head section 10. The guide hole 19 downwardly extends from the inner bottom surface 17 of the head section 10 to a lower end of a screw section 20 through an inner portion of the screw section 20.

Figure 5:
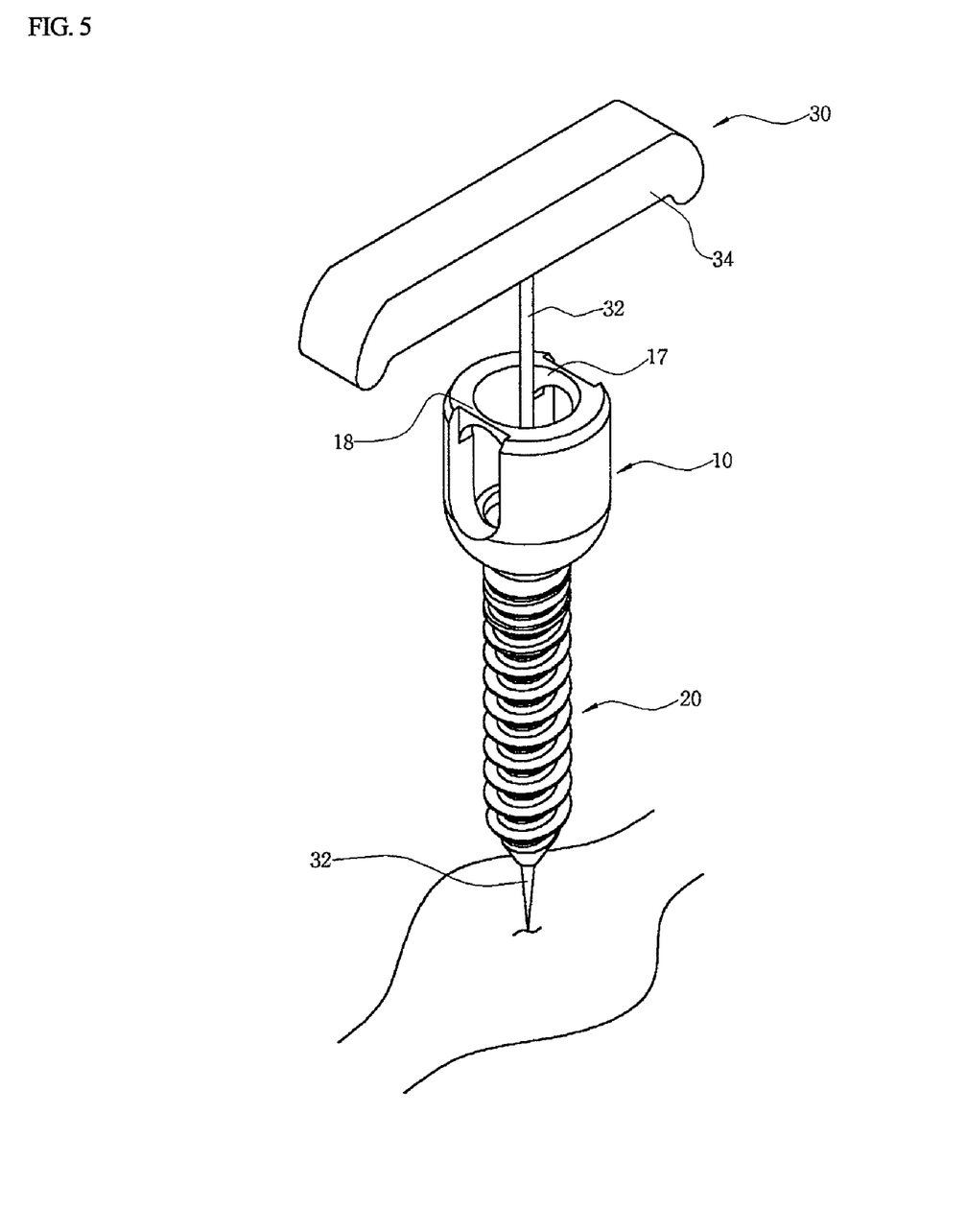
FIG. 5 is a perspective view showing usage of a pedicle screw according to one embodiment of the present invention.

FIG. 5 is a perspective view showing usage of a pedicle screw according to one embodiment of the present invention. Referring to FIG. 5, the pedicle screw is located at a precise position of the spine by means of a position indication driver 30.

The position indication driver 30 has a handle 34 and an elongated needle 32 extending downward from the handle 34. The elongated needle 32 is inserted into the guide hole 19 by passing through the screw hole 17 of the recess 14.

The elongated needle 32 downwardly protrudes beyond a lower end of the screw section 20 of the pedicle screw and makes contact with the spine. When the elongated needle 32 is moved into a precise position of the spine by moving the position indication driver 30, the pedicle screw is also located in the precise position of the spine. In this state, the pedicle screw is inserted into the spine by rotating the pedicle screw.

After that, the position indication driver 30 is separated from the pedicle screw by upwardly pulling the position indication driver 30.

Thus, it is not necessary for the operator to move the pedicle screw while enlarging an incision part in order to find a coupling position of the pedicle screw with regard the spine because the elongated needle 32 can point the coupling position of the pedicle screw. The pedicle screw is rotatably inserted into the spine by means of a separate driver (not shown).

Figure 6:
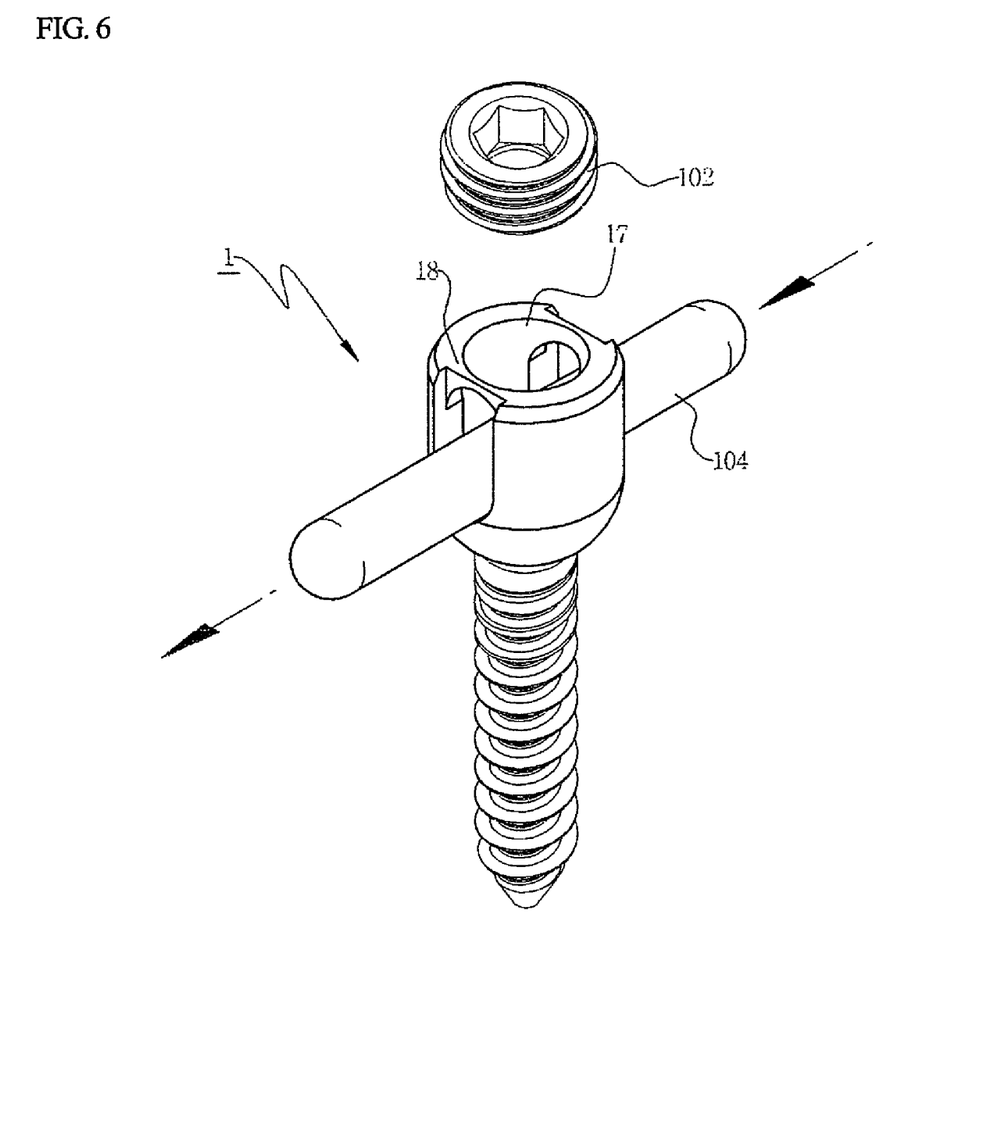
FIG. 6 is a perspective view showing usage of a pedicle screw according to one embodiment of the present invention.

FIG. 6 is a perspective view showing usage of a pedicle screw 1 according to one embodiment of the present invention. Referring to FIG. 6, the rod 104 is inserted into the pedicle screw 1 from a lateral portion of the pedicle screw 1. In this case, the rod 104 is prevented from being separated upwardly from the pedicle screw 1 due to the support unit even if the operator does not conduct any additional procedures.

When the rod 104 has been inserted into the recess 14 from the lateral portion of the recess 14, the coupling screw 102 is screw-coupled into the screw hole 17 while pressing the rod 104 downward. Since the rod 104 is prevented from upwardly moving from the recess 14, it is necessary to push the rod 104 in the lateral di on when removing the rod 104 from the recess 14.

In short due to the support unit 18, the rod 104 inserted into the recess 14 is prevented from being separated from the recess 104 even if the coupling screw 102 has not been screw-coupled with the recess 14, so the operator can easily perform the surgical operation.

Although it is described that the head section of the pedicle screw is integrally formed with the screw section, the present invention can be applicable for a multi-axial pedicle screw in which a head section is separated from a screw section so that the screw section can move with regard to the head section.

Figure 7:
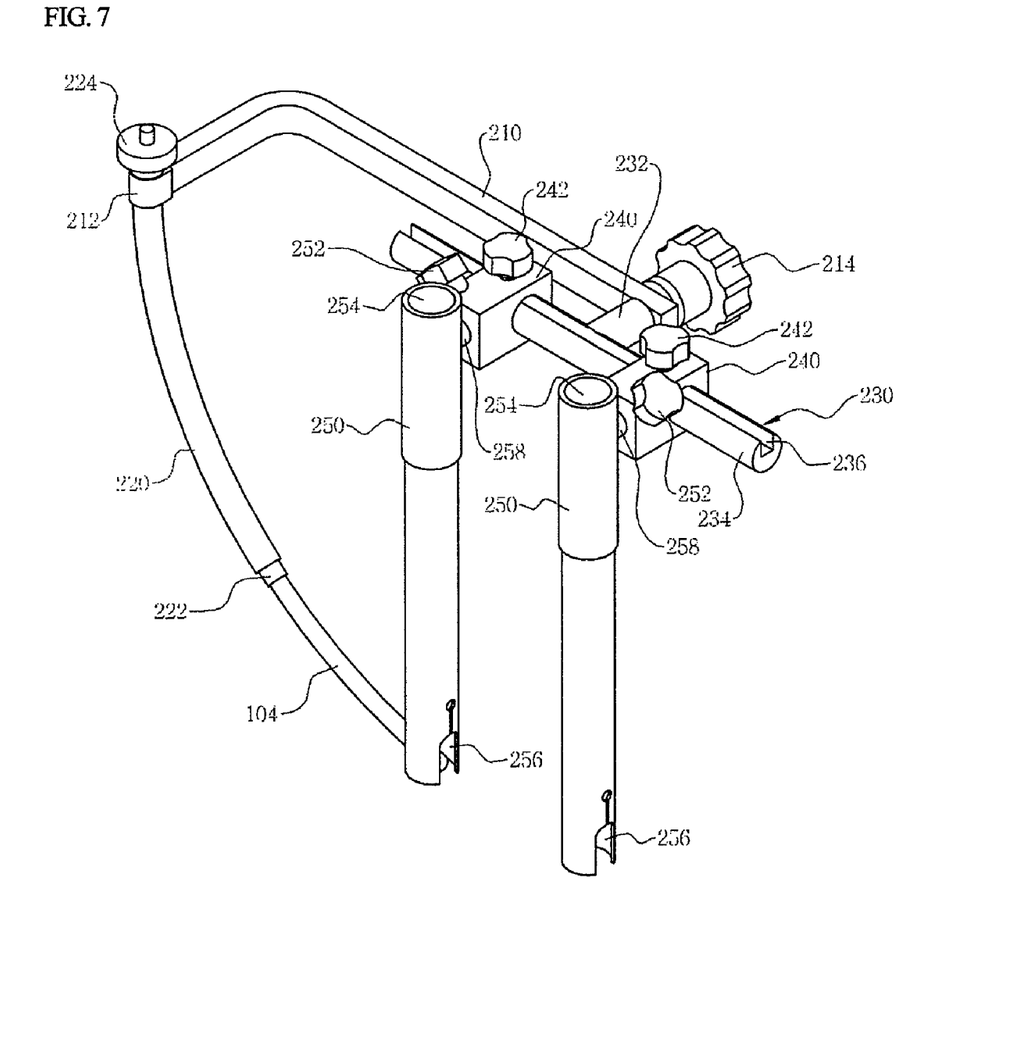
FIG. 7 is a perspective view showing an operating device for a pedicle screw according to one embodiment of the present invention.
Figure 8:
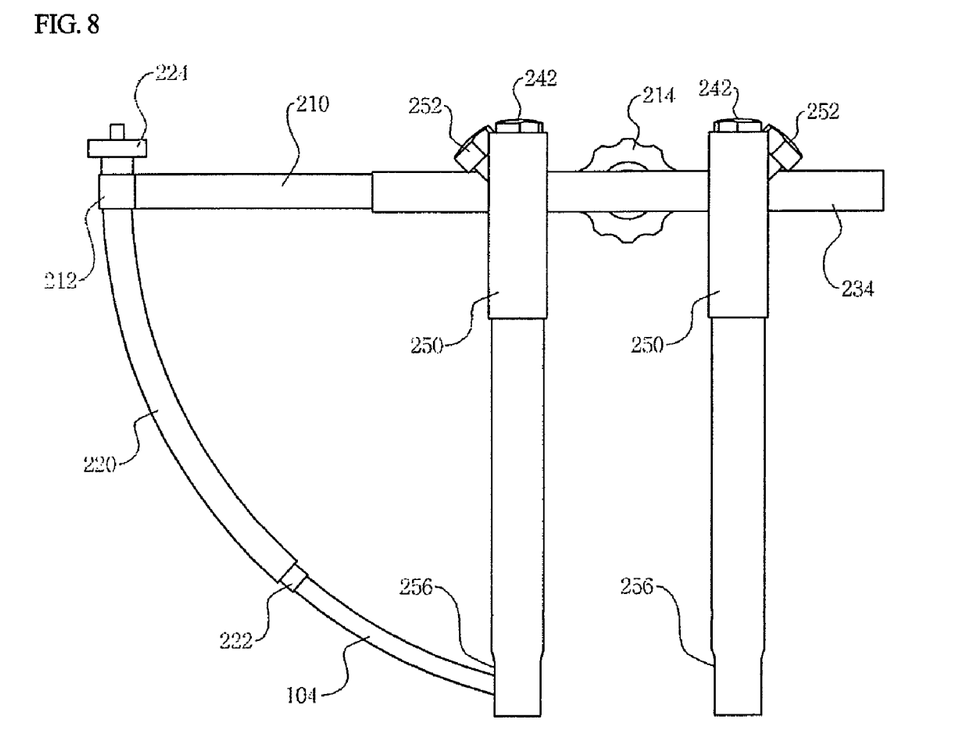
FIG. 8 is a front view showing an operating device for a pedicle screw according to one embodiment of the present invention.
Figure 9:
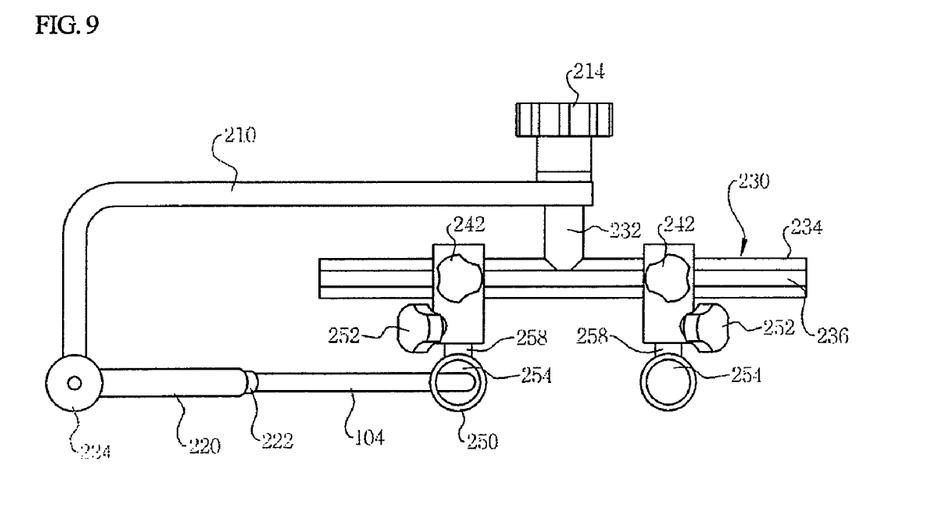
FIG. 9 is a plan view showing an operating device for a pedicle screw according to one embodiment of the present invention.

FIG. 7 is a perspective view showing an operating device for a pedicle screw according to one embodiment of the present invention, FIG. 8 is a front view showing the operating device for the pedicle screw, and FIG. 9 is a plan view showing the operating device for the pedicle screw. Referring to FIG. 7 to 9, the operating device for the pedicle screw includes a body 230, a rotating member 210 rotatably coupled to a rear portion of the body 230, at least two screw coupling rods 250 vertically coupled to a front portion of the body 230, and a rod receiver 220 provided at a second end 212 of the rotating member 210 in the form of a curved rod and extends toward a lower end of the screw coupling rods 250.

The rotating member 210 preferably has a reverse "L" shape and a first end of the rotating member 210 is coupled to the rear portion of the body 230 through a rotary screw shaft 214 such that the rotating member 210 can rotate about the rotary screw shaft 214. The second end 212 of the rotating member 210 is formed with a hole so as to receive the rod receiver 220 therein. As the rotating member 210 rotates, the rod receiver 220 is also moved in up and down directions.

An upper end portion of the rod receiver 220 is coupled with the second end 212 of the rotating member 210. In addition, the rod 104 is detachably coupled with a lower end portion of the rod receiver 220. The rod receiver 220 has a curved structure in the form of an arc having a predetermined curvature. As the rotating member 210 rotates, the rod receiver 220 also rotates along a predetermined circular route. Preferably, the rod 104 inserted into the lower end portion of the rod receiver 222 has a curved structure with a predetermined curvature identical to the curvature of the rod receiver 220. Reference numeral 224 represents a fastening screw 224.

The rotating member 210 is connected to the screw coupling rod 250 through the body 230. Preferably, the body 230 has a "⊦"-shaped structure when looking at the body 230 from the upper region of the body 230. The body 230 is provided at a middle portion thereof with a central protrusion 232 and one end of the rotary screw shaft 214 is inserted into the central protrusion 232 while interposing the first end of the rotating member 210 therebetween. The body 230 includes an elongated rod 234. The central protrusion 232 is provided at a middle portion of the elongated rod 234. A coupling slot 236 is longitudinally formed along an upper portion of the coupling screw 234. At least two screw coupling rods 250 are vertically coupled to the elongated rod 234 in such a manner that the angel of the screw coupling rods 250 can be slightly adjusted.

The screw coupling rod 250 has a hollow pipe shape and an upper end of the screw coupling rod 250 is coupled to the elongated rod 234. A pedicle screw (not shown) is inserted into a lower end of the screw coupling rod 250. The screw coupling rod 250 is formed with a perforated hole 254. A driver (not shown) may be inserted into the perforated hole 254 of the screw coupling rod 250 in order to manipulate the pedicle screw. Preferably, a rod hole 256 is formed at a lower lateral portion of the screw coupling rod 250. The rod hole 256 receives a head section of the pedicle screw. That is, as the rotating member 210 rotates, the rod 105 inserted into the second end 222 of the rod receiver 220 is introduced into the head section of the pedicle screw by passing through the rod hole 256. Coupling members 240 are provided to couple the screw coupling rods 250 to the elongated rod 234 of the body 230. Each of the coupling members 240 has a hexahedral structure and the elongated rod 234 of the body 234 passes through the coupling member 240. In addition, a protrusion 258 of the screw coupling rod 250 is inserted into the coupling member 240. A first screw 242 is screw coupled into the coupling member 240 in order to fix the elongated rod 234 and a second screw 252 is screw coupled into the coupling member 240 in order to fix the protrusion 258 of the coupling rod 250.

The first screw 242 is inserted into the coupling slot 236 of the elongated rod 234. The first screw 242 extends toward an inner portion of the coupling member 240 by passing through an upper surface of the coupling member 240 so that an end portion of the first screw 242 is inserted into the coupling slot 236 of the elongated rod 234. When releasing the first screw 242, the coupling member 240 can move along the elongated rod 234. In addition, the coupling member 240 can be fixed to predetermined portion of the elongated rod 234 when fastening the first screw 234.

The second screw 252 is screw-coupled into the coupling member 240 in order to adjust a rotational angle or a gradient of the screw coupling rod 250. The protrusion 258 inserted into the coupling member 240 is provided at an upper end portion of the screw coupling rod 250 and the second screw 252 makes contact with the protrusion 258 of the screw coupling rod 250 by passing through the coupling member 240.

The protrusion 258 has a cylindrical shape and is rotatably inserted into the coupling member 240. As the protrusion 258 rotates, the screw coupling rod 250 is slightly moved by a predetermined angle. Thus, a position of the screw coupling rod 250 is adjusted in a state that the second screw 252 is slightly released. Then, the second screw 252 is fastened such that the second screw 252 fixedly presses the protrusion 258, so the position of the screw coupling rod 250 is fixed with respect to the body 230.

Figure 10:
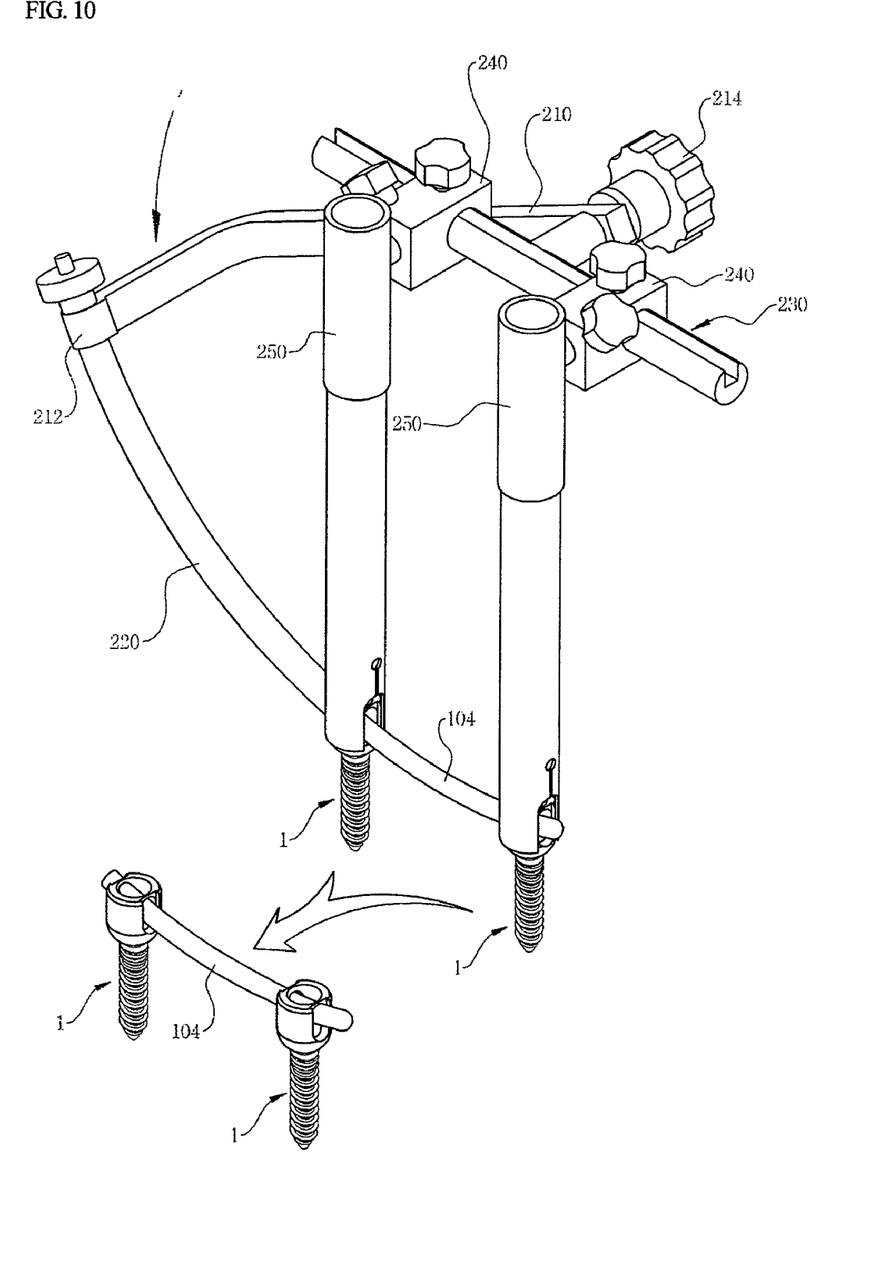
FIG. 10 is a perspective view showing an operational state of an operating device for a pedicle screw according to one embodiment of the present invention.

FIG. 10 is a perspective view showing an operational state of the operating device for the pedicle screw according to one embodiment of the present invention. Referring to FIG. 10, the pedicle screw 1 is inserted into a lower portion of the screw coupling rod 250. In this state, the rod 104 is inserted into the pedicle screw 1 by rotating the rotating member 210 in the downward direction.

That is, the pedicle screw 1 is coupled with the screw coupling rod 250 and the position of the body 230 is determined according to the position of the screw coupling rod 250. As the rotating member 210 coupled with the body 230 rotates in the downward direction, the rod receiver 220 and the rod 104 connected to the second end 212 of the rotating member 210 may be directed toward the rod hole 256 formed at the lower end portion of the screw coupling rod 250.

Thus, the operator can easily insert the rod 104 into the pedicle screw 1 without performing additional inspection work by simply rotating the rotating member 210 in the downward direction thereof. Therefore, if two incisions for two pedicle screws 1 and one incision for the rod 104 and the rod receiver 220 are made in the back of the patient, the rod 104 can be easily inserted into the pedicle screw 1.

When the rod 104 coupled with a detachment section 222 of the rod receiver 220 has been placed in the head section of the pedicle screw 1 due to the rotation of the rotating member 210, the coupling screw 102 (see, FIG. 1) is inserted into the perforated hole of the screw coupling rod 250 and the driver is also inserted into the perforated hole of the screw coupling rod 250 in order to fasten the coupling screw 102, thereby fixedly securing the rod 104 to the pedicle screw 1. After that, the rod 104 is separated from the rod receiver 220 and the rotating member 210 is rotated in the upward direction, thereby removing the rod receiver 220 from the back of the patient.

Figure 11:
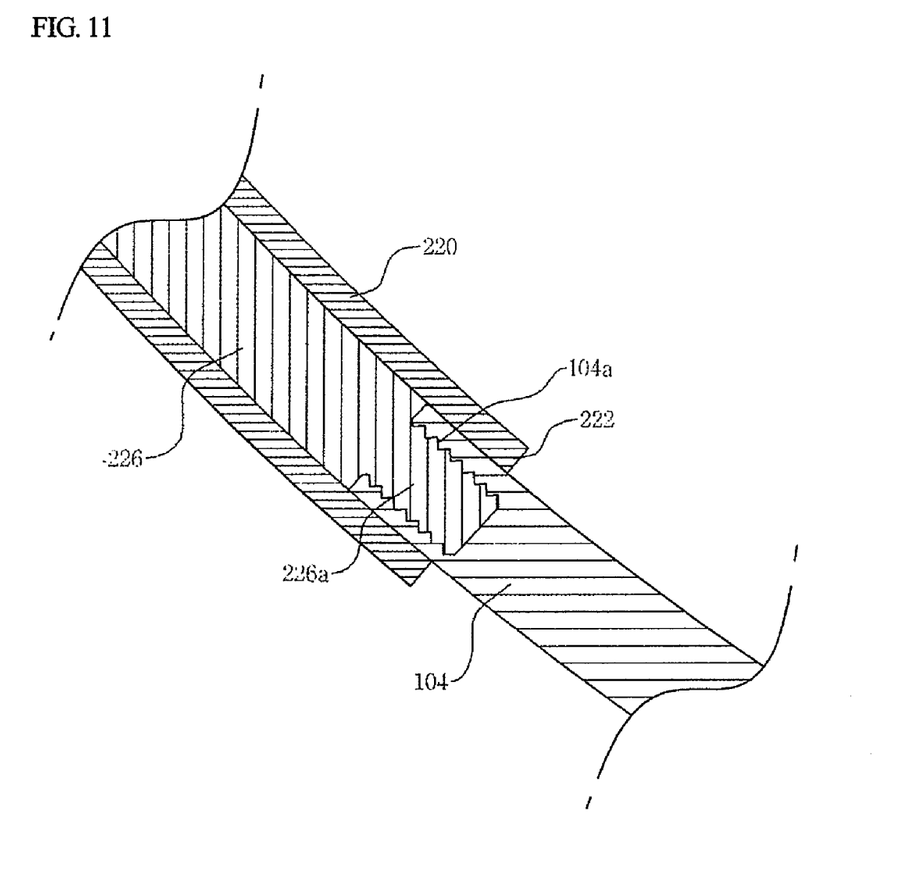
FIG. 11 is an enlarged sectional view showing a rod inserted into a rod receiver according to one embodiment of the present invention.
Figure 12:
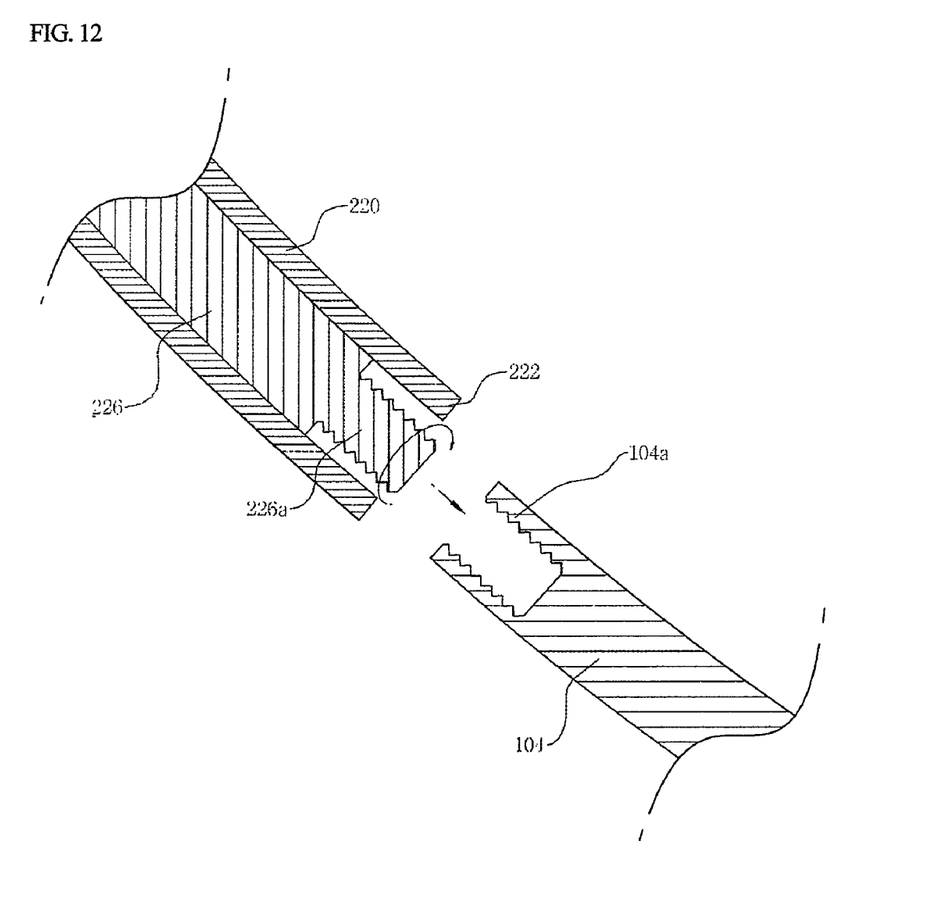
FIG. 12 is an enlarged sectional view showing a rod being separated from a rod receiver according to one embodiment of the present invention.

FIG. 11 is an enlarged sectional view showing the rod inserted into the rod receiver according to one embodiment of the present invention, and FIG. 12 is an enlarged sectional view showing the rod being separated from the rod receiver according to one embodiment of the present invention. Referring to FIGS. 11 and 12, the rod 104 is partially inserted into the detachment section 222 of the rod receiver 220. The detachment section 222 is formed at a lower end portion of the rod receiver 220 in order to detachably receive the rod 104. The rod 104 is formed at one end thereof with a female screw section 104a such that the rod 104 can be screw-coupled with the rod receiver 220. The female screw section 104a is formed at an inner wall part of a hole formed in the rod 104. A flexible shaft 226 is positioned in the rod receiver 220. A male screw section 226a of the flexible shaft 226 is located in the vicinity of the detachment section 222 of the rod receiver 220. The rod 104 has a curved shape in the form of an arc and the female screw section 104a formed at one end of the rod 104 is screw-coupled with the male screw section 226a of the flexible shaft 226.

The flexible shaft 226 is made from a synthetic resin material, such as plastic, which can be easily bent without deforming a shape thereof. An upper portion of the flexible shaft 226 is connected to a fastening screw 224 provided at an upper end portion of the rod receiver 220. As the fastening screw 224 rotates, the flexible shaft 226 also rotates.

The male screw section 226a of the flexible shaft 226 may be coupled with the female screw section 104a of the rod 104 or released from the female screw section 104a of the rod 104 according to a rotational direction of the fastening screw 224. If the flexible screw 226 rotates in one direction as shown in FIG. 8, the rod 104 is separated from the flexible screw 226. Accordingly, the rod 104 can be easily implanted into the spine of the patient through the steps of inserting the rod 104 into a target position in the pedicle screw 1, separating the rod 104 from the flexible screw 226 by rotating the fastening screw 224, and lifting the rotating member 210.

As described above, the pedicle screw according to the present invention has a support unit capable of preventing a rod from being easily separated from the pedicle screw, thereby facilitating minimum incision surgery.

In addition, the pedicle screw according to the present invention is formed with a guide hole, which receives a position indication driver, so the operator can easily detect a precise insertion point of the pedicle screw during minimum incision surgery.

In addition, the present invention provides an operating device for the pedicle screw, capable of implanting a plurality pedicle screws into the body of the patient while making several incisions for the pedicle screws and the rod in the back of the patient and keeping the size of incisions quite a small.

Furthermore, the operating device for the pedicle according to the present invention may allow an operator to easily insert the rod into the pedicle screw inserted into the incision made in the patient's back without checking the location of the pedicle screw and the rod with the naked eye.

In addition, the operating device for the pedicle according to the present invention can easily separate the rod from the pedicle screw after the rod has been inserted into the pedicle screw.

The operating device for the pedicle according to the present invention includes a screw coupling rod, so the number of pedicle screws used for minimum incision surgery may increase without limitation.

Although a preferred embodiment of the present invention has been described for illustrative purposes, those skilled in the art will appreciate that various modifications, additions and substitutions are possible, without departing from the scope and spirit of the invention as disclosed in the accompanying claims.

The present disclosure relates to subject matter contained in Korean Patent Application Nos. 10-2002-0056911, filed on Jul. 21, 2004, and 10-2004-0056912, filed on Jul. 21, 2004, the contents of both are herein expressly incorporated by reference in their entireties.

What is claimed is:

1. A pedicle screw comprising:
   a head section including a recess part defined by first and second sidewalls;
   a screw section; and
   a support unit formed at an upper portion of the recess part of the head section to connect horizontally the upper portions of the first and the second sidewalls, wherein the support unit is formed integrally with the head section thereby allowing a rod to be inserted from the side of the head section into the recess and preventing the rod from being separated upwardly of the recess.

2. The pedicle screw as claimed in claim 1, wherein the pedicle screw has a guide hole extending from an inner bottom surface of the head section to a lower end portion of the screw section.

* * * * *